United States Patent [19]

Amundsen et al.

[11] Patent Number: 4,505,928
[45] Date of Patent: Mar. 19, 1985

[54] PHARMACEUTICAL COMPOSITION CONTAINING CIS-PLATINUM (II) AMINE LACTATE AND A METHOD OF USING SAME

[75] Inventors: Alan R. Amundsen, Somerville; Eric W. Stern, Mountainside, both of N.J.

[73] Assignee: Engelhard Corporation, Iselin, N.J.

[21] Appl. No.: 332,112

[22] Filed: Dec. 18, 1981

Related U.S. Application Data

[60] Continuation-in-part of Ser. No. 178,670, Aug. 18, 1980, abandoned, which is a division of Ser. No. 50,235, Jun. 20, 1979, abandoned.

[30] Foreign Application Priority Data

Jun. 12, 1980 [CA] Canada .................................... 353897
Jun. 18, 1980 [AU] Australia ................................... 59368

[51] Int. Cl.³ ............................................. A61K 31/28
[52] U.S. Cl. .................................................. 514/492
[58] Field of Search ......................................... 424/287

[56] References Cited

U.S. PATENT DOCUMENTS 4,115,418  9/1978  Gale et al. ...................... 260/429 R
4,140,707  2/1979  Clearg et al. ................... 260/429 R Primary Examiner—Jerome D. Goldberg

[57] ABSTRACT

A pharmaceutical composition having as the active ingredient a cis-platinum(II) amine lactate complex in which said amine is derived from ammonia or a monodentate or bidentrate amine ligand such as an alkylamine or alkylene diamine. Said compositions may be administered orally or parenterally and they exhibit pronounced activity against malignant animal tumor cells sensitive thereto.

23 Claims, 6 Drawing Figures

FIG. I.

IR SPECTRUM OF $[Pt(NH_3)_2(LACTATE)_2]$

IR SPECTRUM OF $[Pt(CH_3NH_2)_2(LACTATE)_2]$

NMR SPECTRUM OF $[Pt(MeNH_2)_2(LACTATE)_2]$

IR SPECTRUM OF $[Pt(en)(LACTATE)_2]$

NMR SPECTRUM OF [Pt(en)(LACTATE)₂]

UV SPECTRUM OF THREE [Pt A₂(LACTATE)₂] COMPOUNDS

A. A=NH₃
B. A=CH₃NH₂
C. A₂=en

PHARMACEUTICAL COMPOSITION CONTAINING CIS-PLATINUM (II) AMINE LACTATE AND A METHOD OF USING SAME

This is a continuation-in-part of applicants' copending application Ser. No. 178,670 filed Aug. 18, 1980, now abandoned, which is a Division of Application Ser. No. 50,235 filed June 20, 1979, now abandoned.

This invention relates to a pharmaceutical composition in which the active ingredient is a lactate complex of a platinum(II) amine wherein the amine moiety is derived from ammonia, a monodentate amine or a bidentate amine. Said complex corresponds to the general formula: cis-[PtA$_2$-lactate)$_2$] wherein A is ammonia or an alkylamine such as methylamine and A$_2$ is a bidentate alkylenediamine such as ethylenediamine. These complexes are characterized by high water solubility, a pronounced activity against certain malignant animal tumors sensitive thereto and low animal toxicity.

BACKGROUND

Figure 1:
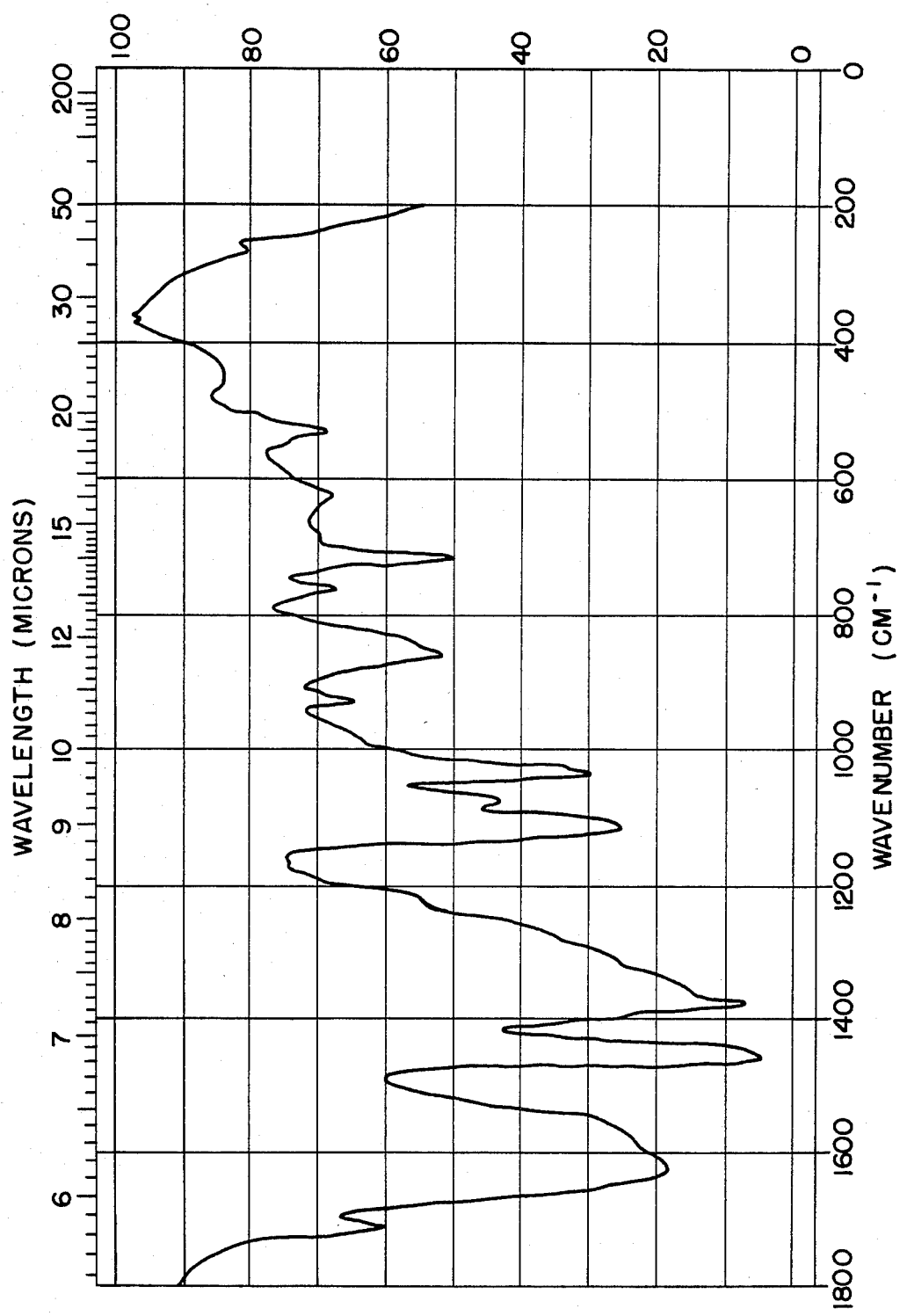
FIG. 1 is a reproduction of the infrared spectrum of the diammine cis-platinum(II) lactate complex of Example 1.

Rosenberg and Van Camp have reported that certain platinum coordination compounds are of interest as potential anti-tumor agents (Rosenberg and Van Camp; "Platinum Compounds: A New Class of Potential Anti-Tumor Agents", Nature, Vol. 222: 385-386 (1969)). This discovery has led to the extensive testing of platinum and other transition metal compounds for similar activity. See in this regard M. J. Cleare; "Transition Metal Complexes in Cancer Therapy", Coordination Chemistry Reviews, Vol. 12: 349-405 (1974). A platinum lactate complex comprised of 1,2-diaminocyclohexane has also been reported as effective against L1210 leukemia in mice (Ridgway et al.; "Analogs of Sulfato 1,2-Diamino-cyclohexane Platinum(II); Modifications in a Leaving Ligand", Journal of Clinical Hematology and Oncology, Vol 7: [No. 1], 220 (1977), and Speer et al.; "Angalogs of Malonato 1,2-Diaminocyclohexane Platinum(II) as Potential Anti-Tumor Agents", Journal of Clinical Hematology and Oncology, Vol. 7: [No. 3], 856 (1977)).

J. L. Marx reports that complexes corresponding to the formula: cis-[PtA$_2$X$_2$] wherein A is an amino moiety and X is an anion, exhibit anti-tumor activity although they are not as a class very soluble. (J. L. Marx; Science, Vol. 192: 774 (1976)). Solubilities observed in water or saline at 37° C. range from 0.04 g/100 ml for cis-[Pt(NH$_3$)$_2$ (malonate)] to 1.38 g/100 ml for cis-[Pt(CH$_3$NH$_2$)$_2$Cl$_2$] (Cleare and Hoeschele; Bioinorganic Chemistry, Vol. 2: 187 (1973)). Low water solubility greatly reduces the compounds' utility for oral or intravenous administration. By contrast, the complexes of the present invention are highly soluble in water (greater than 10 g/100 ml when freshly prepared) and, they may be administered both orally and parenterally.

SUMMARY OF THE INVENTION

This invention provides pharmaceutical compositions in which the active ingredient is a lactate complex of platinum(II) coordinated to two monodentate amine moieties or one bidentate amine moiety. These complexes are highly soluble in water when freshly prepared and they are soluble to an extent greater than 10 g. per 100 ml. of water at room temperature. All compounds exhibit excellent anti-tumor activity against malignant animal tumor cells sensitive thereto and, in addition, they possess low mammalian toxicity. As a consequence, the complexes of this invention possess a more favorable therapeutic index than previously known anti-neoplastic platinum (II) complexes.

The platinum(II) complexes of this invention may be represented by the general formula:

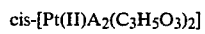

wherein A is ammonia (NH$_3$) or a monodentate alkylamine of the formula RNH$_2$ where R is hydrogen or lower alkyl; A$_2$ is a bidentate diamine moiety represented by the general formula:

wherein each of R$^1$ and R$^2$, taken separately, represent hydrogen or lower alkyl and C$_3$H$_5$O$_3$ represents the lactate anion. As herein employed the term "lower alkyl" is meant to include linear or branced chain alkyl groups of from about 1-6 carbons and, preferably, an alkyl of from about 1-3 carbons. Illustrative amines include, for example, methylamine, ethylamine, propylamine, isopropylamine, ethylenediamine, 1,2-propylenediamine and the like among which ethylenediamine is preferred.

The lactate moiety, (C$_3$H$_5$O$_3$), has the following optically active isomeric structures:

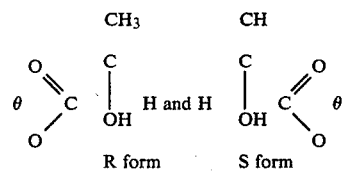

R form    S form where ⊖ signifies that the attached group is above the plane of the paper and signifies that the attached group is below the plane of the paper. The lactate moiety of the complex [PtA$_2$(C$_3$H$_5$O$_3$)$_2$] can be derived from either of the optically active lactate isomers or from a racemic mixture.

The complexes of this invention are prepared by reacting the corresponding amine complexed diaquo-cis-platinum(II) salt with a lactate salt in aqueous medium.

The "diaquo" salt is represented by the formula:

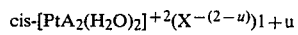

wherein $A_2$ is as defined above, X is an inorganic anion and u is 0 or 1. Suitable anions are those which are stable in acid media; they include, for example, the sulfate, nitrate and perchlorate anions although nitrate is preferred. Anions having a greater complexing ability than water or lactate such as chloride, bromide and iodide are not suitable.

The "diaquo" salt is formed from the stoichiometric reaction of the dichloro-cis-platinum amine complex with a silver salt, preferably, silver nitrate in an aqueous medium at room temperature. Although room temperatures are preferred for this reaction, higher or lower temperatures may be employed as, for example, from about 0° C. to about 50° C. The "diaquo" salt is unstable in solution but it may be converted to the solid and stable cis-$[PtA_2(OH)]_2(NO_3)_2$ by reaction with one gram mole of base per gram atom of platinum. The resulting dimeric complex may be reconverted to its monomer form with acid or it may be used directly in the preparation of the lactate compounds.

The lactate salts are water soluble salts, preferably, alkali metal lactate salts such as sodium or potassium lactate. The diaquo salt solution is reacted with the lactate salt in an aqueous medium, preferably, in stoichiometric amounts, that is, in quantities of about 2 moles of lactate ion per gram atom of platinum. In general, a ratio of from about 1.8 to about 2.2 equivalents of lactate per gram atom of platinum is desirable. The concentration of the reactants in the aqueous medium is not particularly critical; however, it is preferred that the concentration of platinum be maintained at approximately 0.2 molar, i.e., from about 0.1 to about 0.3 molar. Preferably, the mixture is stirred at ambient temperature for a period of time to facilitate the reaction. If desired, temperatures above or below ambient temperature as, for example, from about 0° C. to 50° C., may be employed. The period of reaction can vary from several minutes to several hours depending upon the nature of the reactants and the reaction temperature. The high water solubility of cis-$[PtA_2(C_3H_5O_3)_2]$ coupled with the low affinity of Pt(II) for monodentate carboxylates makes it difficult to isolate cis-$[PtA_2(C_3H_5O_3)_2]$ from this reaction mixture.

The complexes of this invention may also be prepared from cis-$[PtA_2Cl_2]$ by reaction with a metal lactate salt such as silver lactate in an aqueous or alcoholic medium:

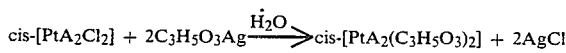

The metal lactate salt is present in the reaction mixture in stoichoimetric amounts, that is, in a ratio of about 2 moles of lactate salt to one mole of cis-platinum amine chloride. The reaction medium is aqueous or alcoholic, preferably, methanolic or ethanolic. The mixture is stirred at ambient temperature for an extended period but higher or lower temperatures within the range of from about 0° C. to about 70° C. may also be employed. When the reaction is carried out in a methanolic medium the mixture is heated to about 60° C. and stirred for about an hour following which the mixture is cooled to ambient temperature. The metal chloride by-product of this reaction may be removed by centrifugation or filtration and the filtrate is evaporated to dryness, preferably, at room temperature. If desired, the cis-$[PtA_2(C_3H_5O_3)_2]$ thus obtained may be recrystallized from a mixture of water, ethanol and acetone. When A is $NH_3$ this procedure is most preferably conducted in an alcoholic solvent in which cis-$[PtA_2(C_3H_5O_3)_2]$ is soluble as, for example, in methanol. Thereafter, this solvent can be removed by conventional means as, for example, by evaporation under vacuum and the residue is recrystallized from an alcohol-acetone mixture. This procedure generally affords a higher yield of product and requires less reaction time than the di-aquo process hereinbefore described.

The complexes of this invention are useful in the treatment of tumors in animals which tumor cells are sensitive to said complexes as, for example, Sarcoma 180 ascites tumors and L1210 lymphoid leukemia tumor cells in mammals such as mice. The anti-tumor cell effect exhibited by the subject complexes may also extend to other sarcomas and lymphoid leukemias and to such other tumors as the following: lymphosarcoma, myelocytic leukemia, malignant lymphona, squamos cell carcinoma, adenocarcinoma, scirrhous carcinoma, malignant melanoma, seminoma, teratoma, choriocarcinoma, embryonalcarcinoma, cystadenocarcinoma, endometroidcarcinoma or neuroblastoma and the like. In addition, said complexes may be useful as anti-viral, anti-inflammatory, anti-bacterial and anti-parasitic agents.

They may be administered parenterally or orally in admixture with a non-toxic pharmacologically acceptable inert carrier or diluent in any of the usual pharmaceutical forms. These include solid and liquid oral unit dosage forms such as tablets, capsules, powders and suspensions or solutions and suspensions for subcutaneous, intramuscular, intravenous or intra-arterial injection. The term "unit doage" refers to physically discrete units which may be administered in single or multiple dosages each containing a predetermined quantity of the active ingredient in association with the required diluent, carrier or vehicle. The quantity of active ingredient is the amount of a complex of this invention which is needed to product the desired therapeutic effect.

A typical unit dosage consists essentially of from about 4–300 mg. of active ingredient; however, the form in which said ingredient is administered and the frequency of administration is usually determinative of the concentration. Thus, for example, oral unit dosage forms containing 4–300 mg. of active ingredient may be administered one or more times per day depending upon the severity of the malignant animal tumor cells which are sought to be treated and the condition of the host animal. By contrast, parenteral administration generally requires from about 10–100 mg. of the active ingredient per unit dosage administered as a daily dose or as a fraction thereof depending upon whether the regimen calls for administration once, twice, three or four times daily.

By contrast to the "unit dosage", the effective dose is that dosage which is needed to achieve the desired anti-malignant animal tumor cell effect. In general, this dosage lies within the range of from about 1–750 mg. of the active ingredient per kg. of body weight of the host animal. A preferred concentration lies within the range of from about 15–120 mg./kg. of body weight. For oral administration it has been found that an effective dose of 80–750 mg./kg. is most suitable, whereas, in the case of parenteral administration it is usually advisable to employ from about 1–200 gm./kg. These dosages are well below the toxic or lethal dose and they may be varied over a wide range for adjustment to the host animal which is being treated.

In this invention the term "pharmacologically acceptable inert carrier or diluent" denotes a non-toxic substance which, when mixed with the active ingredient, renders it more suitable for administration. Compositions intended for oral administration may include such carriers or diluents as glucose, lactose, sodium or potassium lactate, sucrose, corn starch, potato starch, sodium carboxymethyl cellulose, ethyl cellulose, cellulose acetate, powdered gum tragacanth, gelatin, alginic acid, agar, stearic acid or the sodium, calcium and magnesium slats of stearic acid, sodium lauryl sulfate, polyvinylpyrrolidone, sodium citrate, calcium carbonate and dicalcium phosphate. Said compositions may also contain non-toxic adjuvants and modifies such as dyes, buffering agents, preservatives, surfactants, emulsifiers, flavoring agents or biocides and the like.

Tablets are prepared by mixing a complex of this invention in a suitably comminuted or powdered form with a diluent or base such as starch, sucrose, kaolin, di-calcium phosphate and the like. The resulting mixture can be granulated by wetting with a binder such as a syrup, starch (paste), acacia mucilage or solutions of cellulosic or polymeric materials, whereafter, the wetted mixture is forced through a screen. As an alternative to granulating, the powdered mixture can be run through a tablet machine and imperfectly formed slugs broken into granules. The granules are lubricated to prevent sticking to the tablet-forming dies via the addition of stearic acid, a stearate salt, talc or mineral oil and the lubricated mixture is then compressed into tablets. The complexes can also be combined with free flowing inert carriers followed by compression into tablets without going through the granulating or slugging steps. A protective coating or sealing coat of shellac, sugar or polymeric material and a polished coating of wax can also be provided. Dyestuffs may be added to distinguish different unit dosages.

Capsules are formulated by preparing a powdered mixture, as hereinbefore described, and then pouring said mixture into preformed gelating sheaths. A lubricant such as talc, magnesium stearate or calcium stearate can be added as an adjuvant prior to the filling operation. A glidant such as colloidal silica may be added to improve the flow characteristics and a disintegrating or solubilizing agent may also be added to enhance the effectiveness of the medicament upon ingestion.

Powders are prepared by comminuting the compound to a suitable fine size and mixing with a similarly comminuted pharmaceutical diluent or carrier such as an edible carbohydrate as, for example, starch. Sweetening agents and flavorings, preservatives and dispersing and/or coloring agents may also be employed.

Oral fluids such as syrups and elixirs are prepared in unit dosage form so that a given quantity of medicament as, for example, a teaspoonful, contains a predetermined amount of the active ingredient. Suspensions can be formulated by dispersing the active ingredient in a nontoxic vehicle in which it is essentially insoluble.

Fluid unit dosage forms for parenteral administration can be prepared by placing a measured amount of the complex in an ampoule or vial which is sterilized and sealed. An accompanying vial or vehicle can be provided for mixing with said complex prior to administration.

This invention also provides for combining two or more of the subject complexes into a single unit dosage form or, alternatively, combining one or more of said complexes with other known agents useful in the treatment of malignant animal tumor cells, therapeutic agents or nutritive agents and the like so as to enhance or complement the anti-tumor effect against tumor cells which are sensitive to said complexes.

The preferred compositions for oral administration are tablets in which the lactate complex is present in quantities of 25–300 mg. but, preferably, 50–250 mg. in a pharmaceutically acceptable orally ingestible solid carrier. If desired, the composition may also contain flavors, binders, lubricants and other excipients known in the art.

A preferred alternative for oral administration is the soft gelatin capsule. Such a composition may contain from 25–300 mg. but, preferably, 50–250 mg. by weight of active ingredient dissolved or suspended in vegetable oil, peanut oil, alcohol or glycerine and the like.

The following embodiments illustrate representative unit dosage forms.

Compressed Tablet

A tablet suitable for swallowing is prepared by mixing the following ingredients:

| | |
|---|---|
| Cis-[Pt(NH$_3$)$_2$(C$_3$H$_5$O$_3$)$_2$] | 150 mg. |
| Sodium Lactate | 100 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |
| | 430 mg. |

The cis-[(NH$_3$)$_2$(C$_3$H$_5$O$_3$)$_2$], sodium lactate, niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

Soft Gelatin Capsule

A soft elastic gelain capsule is filled with the following ingredients:

| | |
|---|---|
| Cis-[Pt(NH$_3$)$_2$(C$_3$H$_5$O$_3$)$_2$] | 100 mg. |
| Wheat germ oil | 50 mg. |
| Sunflower seed oil | 100 mg. |
| | 250 mg. |

The cis-[Pt(NH$_3$)$_2$(C$_3$H$_5$O$_3$)$_2$] and wheat germ oil are mixed with sunflower seed oil and the resulting mixture is poured into gelatin capsules for oral administration. An alternative embodiment provides for substituting sunflower seed oil and wheat germ oil with equal amounts of peanut oil to obtain an otherwise similar capsule which is also suitable for oral administration.

Dry Filled Capsule

A hard dry-filled capsule may be prepared from the following ingredients:

| | |
|---|---|
| Cis-Diammineplatinum(II) Lactate | 200 mg. |
| Niacinamide | 50 mg. |
| Calcium Pantothenate | 10 mg. |
| Sodium Lactate | 150 mg. |
| | 410 mg. |

The cis-diammineplatinum(II) lactate is reduced to a No. 60 powder. Niacinamide, calcium pantothenate and sodium lactate are passed through a No. 60 bolting cloth and these ingredients are added to the cis-diammineplatinum(II) lactate. This combination of ingredients is mixed for 10 minutes and then poured into a No. 3 size gelatin capsule.

Dry Powder

The following composition illustrates a representative dosage in dry powder form. In this embodiment the active ingredient is water soluble and it is combined with up to 60% by weight of a suitable flavoring agent. All quantities are in a weight-percent relationship.

| | |
|---|---|
| Cis-[Pt(NH$_3$)$_2$(C$_3$H$_5$O$_3$)$_2$] | 25–90% |
| Flavoring Agent | 10–60% |
| Preservative | 0–1.0% |

The cis-[Pt(NH$_3$)$_2$(C$_3$H$_5$O$_3$)$_2$], flavoring agent and preservative are thoroughly blended to afford a homogeneous dry powder which is readily soluble in water. The resulting formulaton may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, groundnut oil, aqueous propylene glycol and a solution of sodium lactate. Typical of said compositions are solutions which contain the active ingredient in sterile form. An embodiment illustrating a dosage form suitable for intravenous injection is set forth below and in Example 4, infra.

Parenteral Solution

Injectable solutions can be formulated by mixing an ampoule of active ingredient with an ampoule of sterile diluent:

| Ampoule: | Cis-[Pt(NH$_3$)$_2$(C$_3$H$_5$O$_3$)$_2$] | 300 mg. |
|---|---|---|
| Ampoule: | Sterile Water (Diluent for Injection) | 2 cc. |

The cis-[Pt(NH$_3$)$_2$(C$_3$H$_5$O$_3$)$_2$] and water are mixed thoroughly immediately prior to administration. If desired, one or more other active ingredients may be added to provide an injectable solution having enhanced therapeutic activity.

Examples 1–3, infra, illustrate the method by which the cis-platinum(II) amine lactate complexes of this invention may be obtained and Example 4 describes the protocol used to evalute their efficacy in animals. However, said examples are illustrative only and this invention should not be construed as being limited thereto because it will be apparent to one of ordinary skill that obvious modifications may be effected and functionally equivalent reagents may be substituted for those recited therein without departing from the spirit or scope of this invention.

EXAMPLE 1

Cis-Diammineplatinum(II) Lactate;
Cis-[Pt(NH$_3$)$_2$(C$_3$H$_5$O$_3$)$_2$]

Procedure A: Cis-[Pt(NH$_3$)$_2$Cl$_2$] (1.5 g) was suspended in water (100 ml) and to it was added a suspension of silver lactate (2.15 g; Ag/Pt=2:1) in water (20 ml). The mixture was stirred at room temperature for 24 hrs. while protected from light. Silver chloride was removed by filtration and washed with water. Filtrate and washings were evaporated to dryness preferably under vacuum at room temperature, leaving a light yellow oil. This was dissolved in a water (7 ml) and ethanol (90 ml) mixture and then acetone (150 ml) was added intermittently while storing the solution in a freezer. After one week the white solid which had formed was filtered, washed with cold ethanol, and vacuum dried at room temperature. The yield of product was 0.74 g (36.4%).

Analysis: cis-[Pt(NH$_3$)$_2$(C$_2$H$_5$O$_3$)$_2$]
Calculated: C, 17.69%, H, 3.93%; N, 6.87%
Found: C, 17.37%; H, 3.30%, N, 6.94%

Procedure B: Cis-[Pt(NH$_3$)$_2$Cl$_2$] (0.3 g) was suspended in methanol (25 ml) and solid silver lactate (0.43 g; Ag/Pt=2:1) added directly. The mixture was warmed to 60° C, then allowed to cool while stirring for one hour. The silver chloride was filtered off, washed with methanol, and the filtrate and washings evaporated to dryness on a rotary evaporator. The residue was dissolved in about 10 ml of methanol and then acetone was added until the solution was cloudy. It was stored in a freezer overnight. The white solid product was filtered, washed with acetone, and vacuum dried. Yield was 0.29 g (71.4%).

Analysis: cis-[Pt(NH$_3$)$_2$(C$_3$H$_5$O$_3$)$_2$]
Calculated: C, 17.69%, H, 3.93%; N, 6.87%
Found: C, 18.93%, H, 3.59%; N, 6.61%

Figure 6:
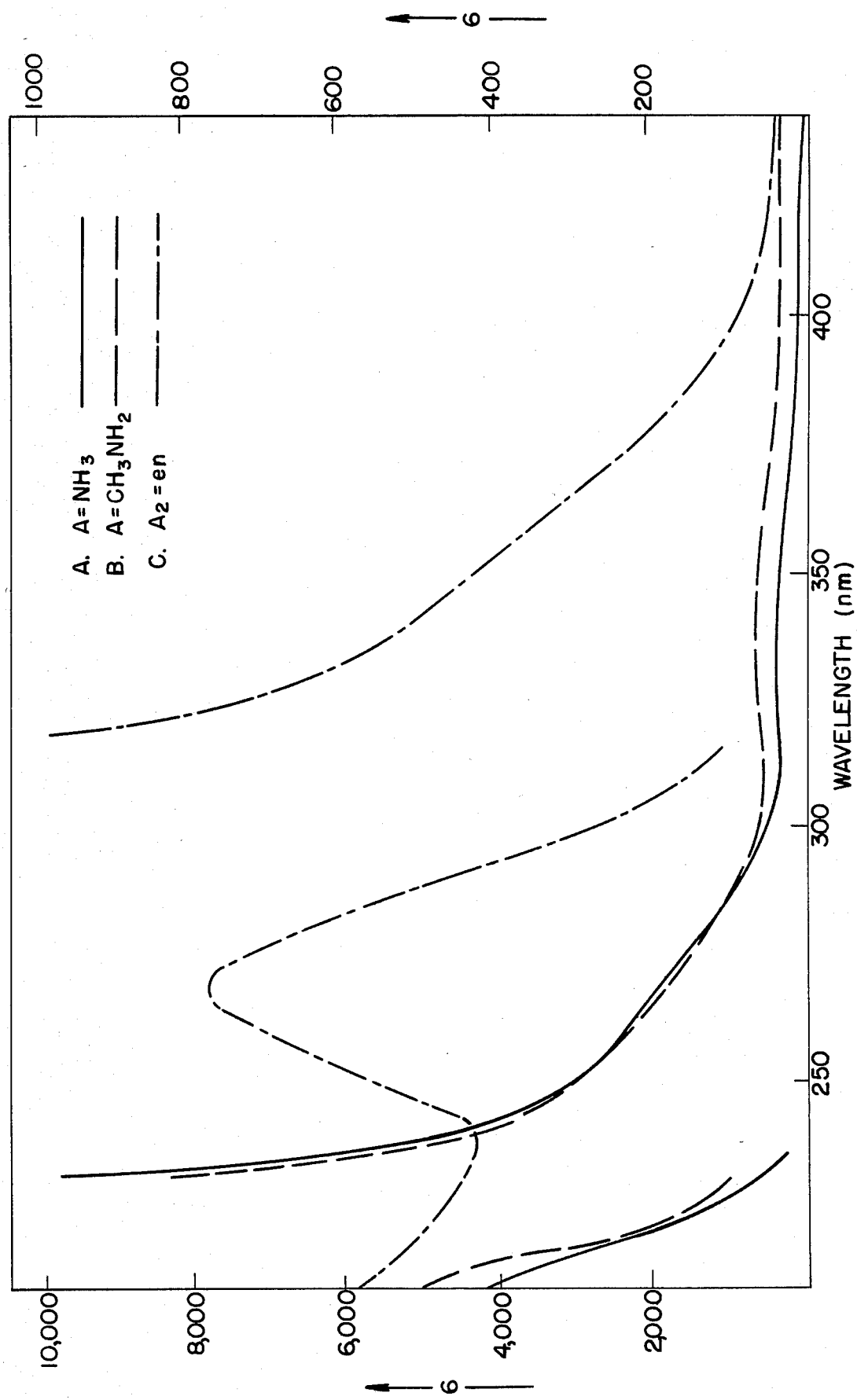
FIG. 6 is a reproduction of the ultraviolet spectra of the complexes described in Examples 1-3.

The infrared spectrum for this complex is reproducted in FIG. 1. The assignments are tabulated in Table I. The ultraviolet spectrum is reproduced as curve A in FIG. 6.

EXAMPLE 2

Cis-Bis(Methylamine)platinum(II) Lactate;
Cis-[Pt(CH$_3$NH$_2$)$_2$(C$_2$H$_5$O$_3$)$_2$]

Cis-[Pt(CH$_3$NH$_2$)$_2$Cl$_2$] (1.065 g) was suspended in water and solid silver lactate (1.396 g; Ag/Pt=2:1) added directly. After stirring overnight while protected from light, the silver chloride was filtered off and washed with water. The filtrate and washings were evaporated to dryness under vacuum at room temperature, leaving a glassy residue. This was dissolved in ethanol (15 ml) and acetone (25 ml) added, and the mixture stored in a freezer overnight. The white solid product was filtered, washed with acetone and ether and vacuum dried. Yield was 0.81 g (57.4%). The product is hygroscopic and will decompose when exposed to light. Therefore, the compound should be stored in a desiccator protected from light.

Analysis: cis-[Pt(CH$_3$NH$_2$)$_2$(C$_3$H$_5$O$_3$)$_2$]
Calculated: C, 22.07%; H, 4.63%; N, 6.43%
Found: C, 22.26%; H, 3.98%; N, 6.33%

Figure 2:
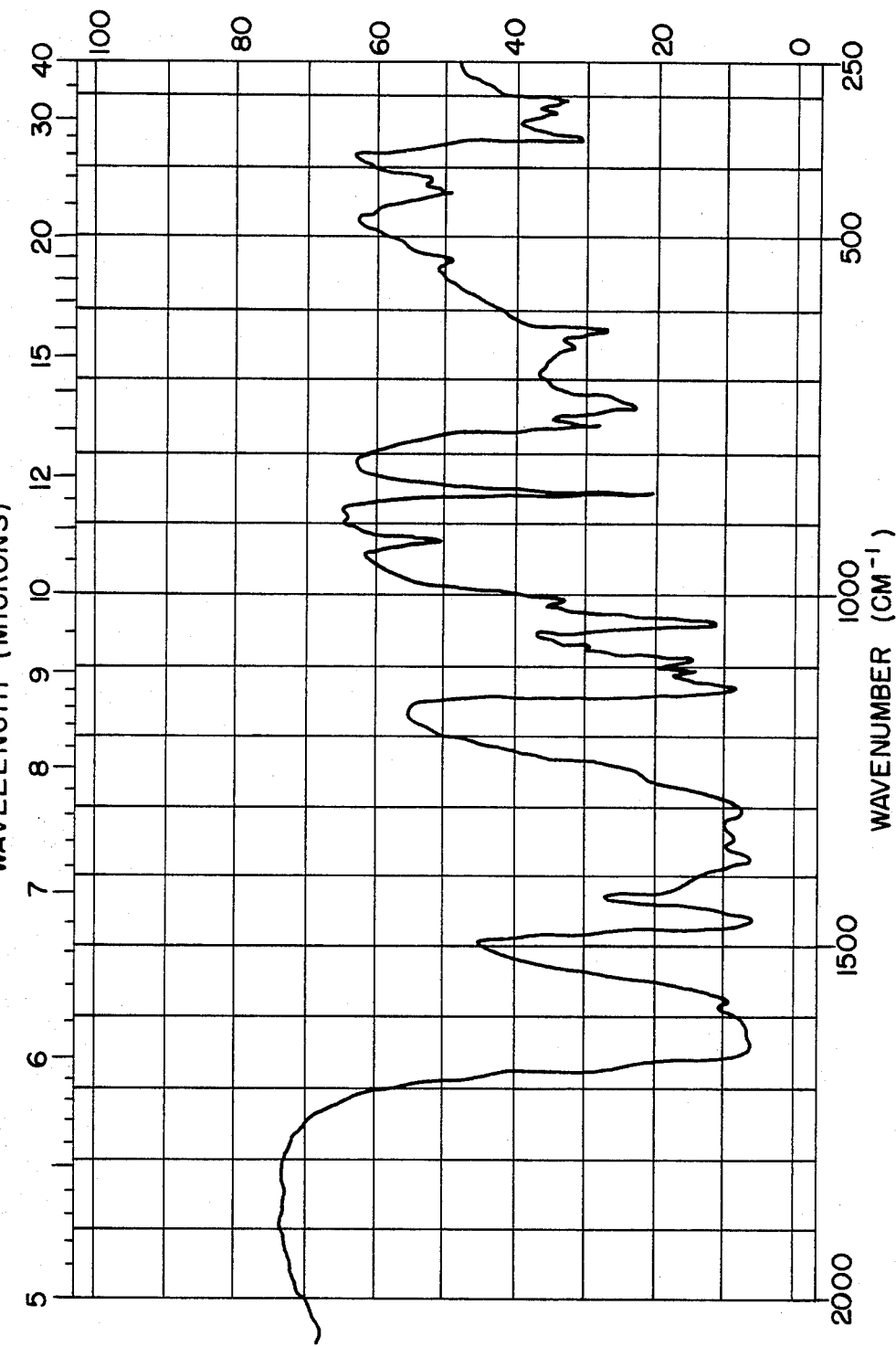
FIG. 2 is a reproduction of the infrared spectrum of the bis-(methylamine)cis-platinum(II) lactate complex of Example 2.
Figure 3:
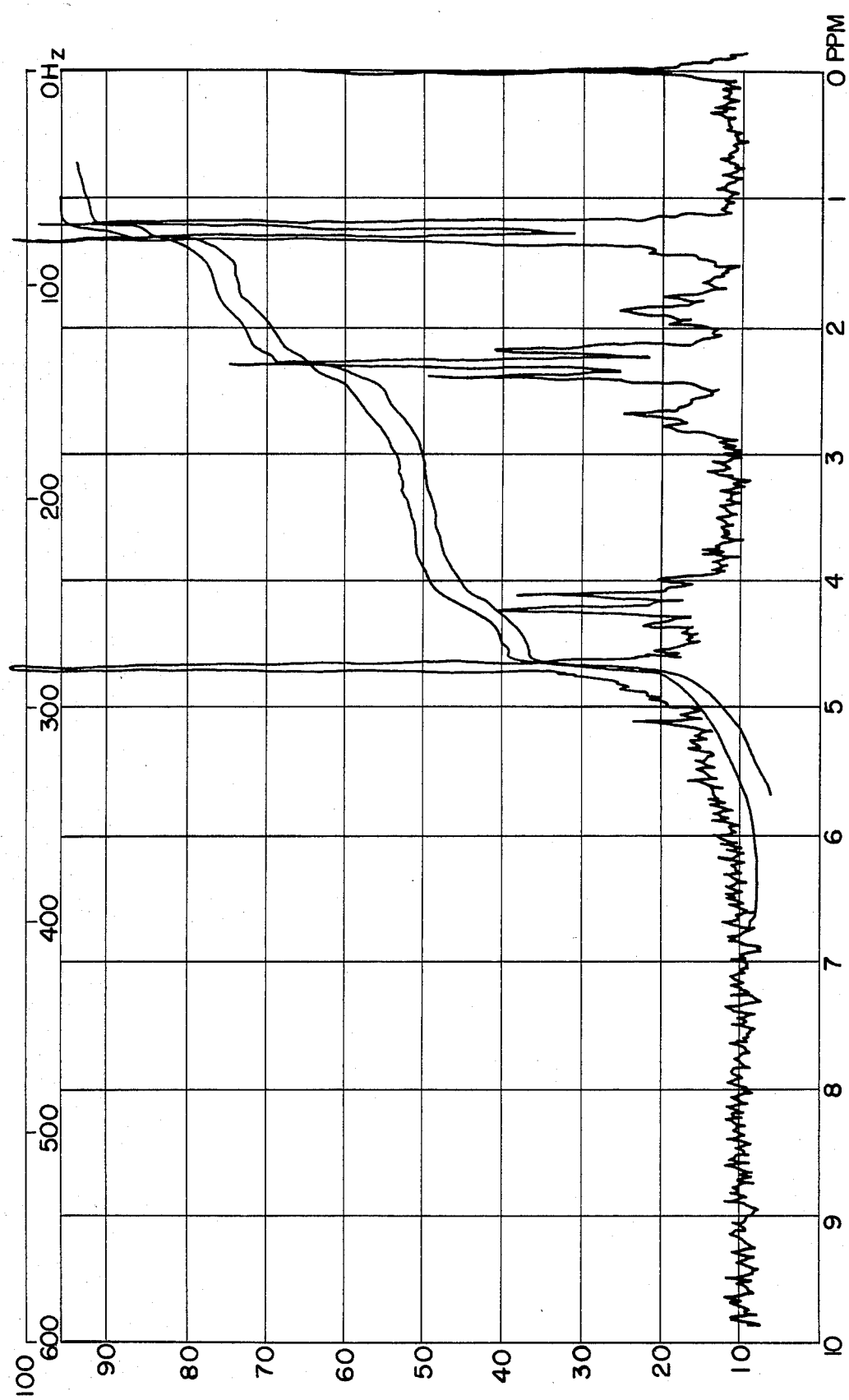
FIG. 3 is a reproduction of the nuclear magnetic resonance spectrum of the bis-(methylamine)cis-platinum(II) lactate complex of Example 2.

The infrared spectrum is reproduced in FIG. 2 and the band assignments are tabulated in Table I. The nuclear magnetic resonance spectrum is reproduced in FIG. 3. The ultraviolet spectrum is reproduced as curve B in FIG. 6.

EXAMPLE 3

Ethylenediamineplatinum(II) Lactate; [Pt(en)(C$_3$H$_5$O$_3$)$_2$]

[Pt(en)Cl$_2$] (3.26 g) was suspended in water and silver lactate (4.3 g; Ag/Pt=2:1) added. (In this Example and hereinafter "en" represents "ethylenediamine"). After stirring overnight while protected from light, silver chloride was filtered off and the filtrate evaporated to dryness under vacuum at room temperature. The residue was dissolved in water, filtered to remove insoluble impurities, and ethanol (10 ml) and acetone (55 ml) added intermittently while cooling in a freezer for about 5 days. The white crystalline product was filtered, washed with acetone, and dried under vacuum. Yield was 3.17 g (73.2%). The product decomposes slowly when exposed to light and should be protected from light when stored.

Analysis: [Pt(C$_2$H$_8$N$_2$)(C$_3$H$_5$O$_3$)$_2$]
Calculated: C, 22.17%; H, 4.19%; N, 6.46%
Found: C, 22.17%; H, 3.49%; N, 6.05%

Figure 4:
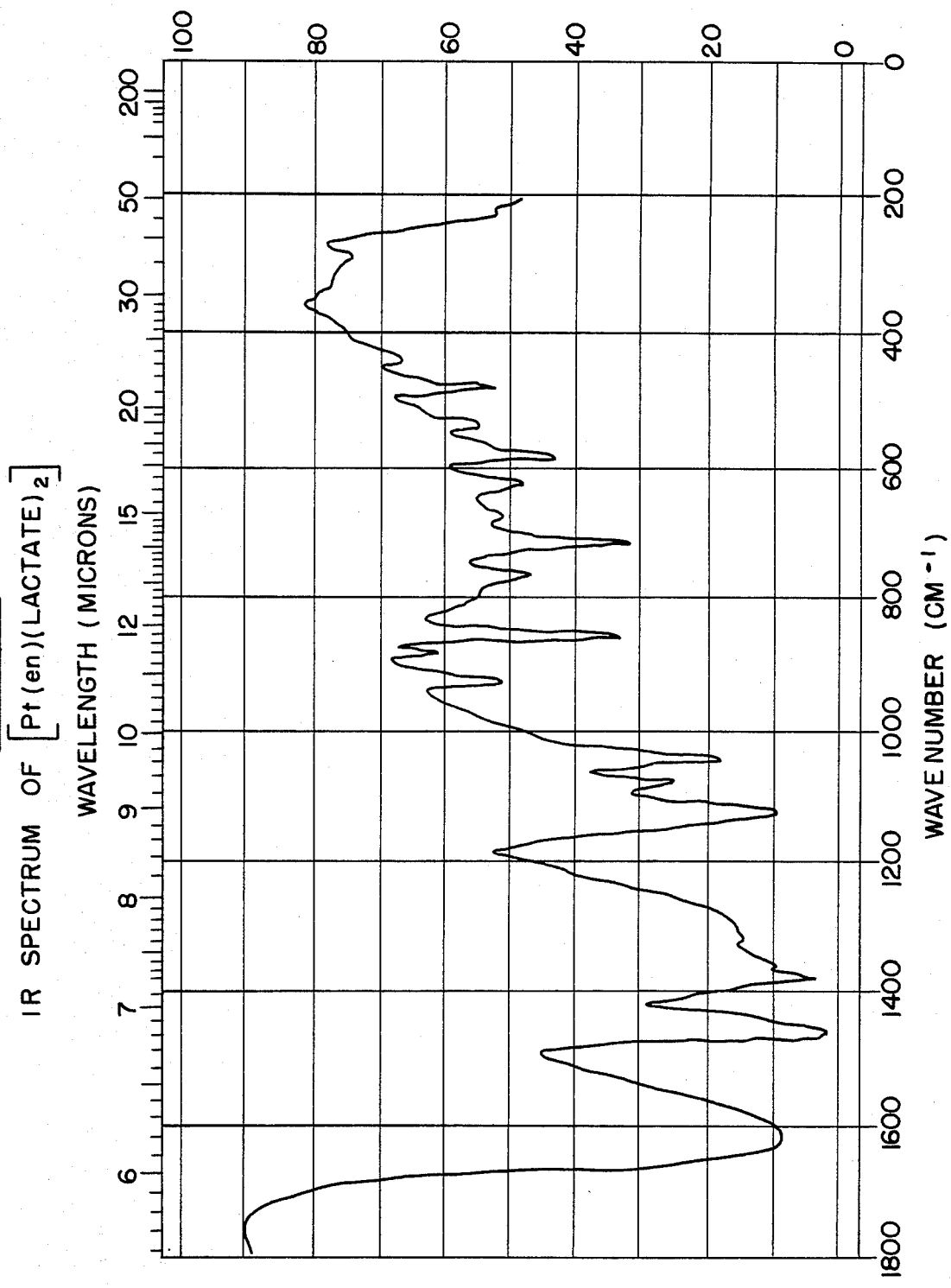
FIG. 4 is a reproduction of the infrared spectrum of the ethylenediamine cis-platinum(II) lactate complex of Example 3.
Figure 5:
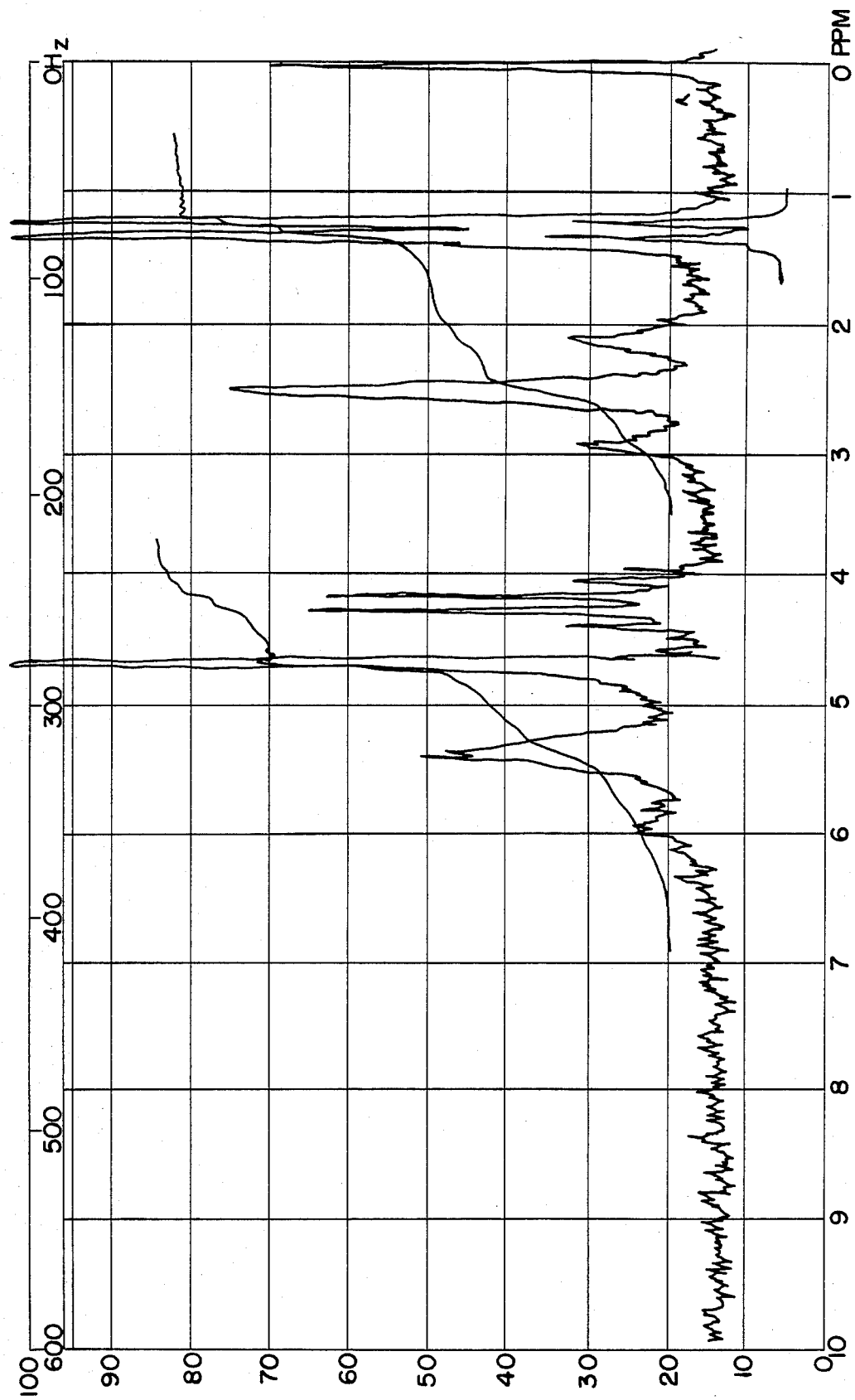
FIG. 5 is a reproduction of the nuclear magnetic resonance spectrum of the ethylenediamine cis-platinum(II) lactate complex of Example 3.

The infrared spectrum is reproduced in FIG. 4 and the band assignments are tabulated in Table I. The nuclear magnetic resonance spectrum is reproduced in FIG. 5. The ultraviolet spectrum is reproduced as curve C in FIG. 6.

EXAMPLE 4

Evaluation of Anti-Tumor Activity

The compounds were evaluated for anti-tumor activity against S180 ascites in female CFW Swiss mice by the following procedure:

CFW mice, averaging 20 g, are immediately inspected and placed in newly prepared cages. On day zero the mice are inoculated with 0.2 ml of the freshly prepared saline suspension (0.15M NaCl) containing $1 \times 10^7$ tumor cells/ml, or a total of $2 \times 10^6$ cells. This inoculum is freshly prepared using "transfer" mice which have been injected with tumor cells the previous week. This inoculum is the end-product of a series of steps which involves (1) the removal of the cells from the peritoneal cavity of the sacrificed transfer mouse, (2) alternate centrifugation-washing (2–3 times with cold saline) to remove occasional blood and other undesirable components, and finally, (3) dilution (1:3) of the packed cell volume with saline (the final centrifugation

TABLE I

| Major Infrared Absorbances of Cis-[PtA$_2$(C$_3$H$_5$O$_3$)$_2$] Complexes[a] | | | |
|---|---|---|---|
| Pt(NH$_3$)$_2$(C$_3$H$_5$O$_3$)$_2$ Example 1 | Pt(CH$_3$NH$_2$)$_2$(C$_3$H$_5$O$_3$)$_2$ Example 2 | Pt(en)(C$_3$H$_5$O$_3$)$_2$ Example 3 | Assignment |
| 3400 sh | 3400 s | 3380 sh | $\nu$OH |
| 3260 s | 3350 sh | 3200 s | $\nu$NH |
| 3170 sh | 3230 s | 3120 sh | |
| 1710 m | | | $\nu$CO$_2$(assym.) |
| 1620 s | 1630 s | 1610 s | $\delta$NH$_2$ |
| 1570 sh | 1600 sh | | |
| 1350 sh | 1335 s | 1350 sh | $\nu$CO$_2$(sym.) |
| 1310 sh | 1290 sh | 1300 sh | $\delta$NH$_2$ |
| 1220 sh | 1240 sh | | |
| 1110 s | 1120 s | 1110 s | Lactate |
| | 1100 m | | |
| 1075 m | 1070 s | 1075 m | Lactate |
| | 1060 w | | |
| 1035 s | 1030 s | 1035 s | Lactate |
| 980 sh | 1000 w | 1000 w | |
| 925 w | 920 m | 925 m | Lactate |
| | | 880 w | |
| 860 m | 850 s | 850 s | |
| 840 sh | | | |
| | | 800 sh | |
| 760 w | 750 m | 760 m | |
| | 640 w | 680 w | |
| 625 w | 620 m | 620 m | |
| | | 580 m | |
| 525 w | 520 w | | $\nu$Pt-N |
| | 500 w | 480 m | |
| | 430 w | 440 m | |
| 440 w | | | $\nu$Pt-O |
| | 410 w | | |

[a]Spectra run as nujol mulls.
Abbreviations: strong; m: medium; w: weak; sh: shoulder.

The following example describes the protocol employed for evaluating the efficacy of the herein-described complexes against tumor cells which are sensitive thereto in a typical animal, a mammal. The preparation of representative dosage forms suitable for intravenous injection are also set forth; however, it will be appreciated by those skilled in the art that said dosage forms are illustrative only and that in practice the dose to be administered will depend ultimately upon the severity of the disease, the age, health and weight of the host which is being treated, the frequency of treatment and the possibility that adverse side effects may occur if other concurrently prescribed therapeutic agents are to be administered.

being carried out at 1,000 rpm for 2 min.). A cell count is made on a 2,000-fold dilution of this 1:3 suspension by means of a Coulter Counter. A final dilution to $1 \times 10^7$ cells/ml is made based on the averaged count. On day 1 solutions of the test compounds are preapared and the mice injected, with each mouse of a set of four mice being injected with the same test compound at the same dose level.

Also, on this day, two types of controls (6 mice/set) are employed: (1) Normal (1 set): 0.5 ml of the solvent medium used for the test compound, and (2) Positive control (1 set): a known anti-tumor agent cis-[Pt(NH$_3$)$_2$Cl$_2$] in saline at 8 mg/kg, used to test the response of the biological system.

The effectiveness of a compound is measured in terms of the increase in life span of the test animal relative to the controls (calculated from the day of tumor inoculation (day zero). In order to standardize the test data and permit intercomparisons to be made, the day of evaluation is arbitrarily taken as that day corresponding to twice the mean life-span (or average day of death) of the normal controls. This sets a practical upper limit of 100% on the ILS attainable. For calculation purposes, survivors on the day of evaluation are considered to have died on that day. The % ILS is formulated as:

$$\% \ ILS = \left( \frac{\text{mean life-span of test mice}}{\text{mean life-span of control mice}} - 1 \right) \times 100\%$$

ILS values above 50% represent significant activity; those above 75% represent excellent activity.

Anti-tumor screening results for cis-[PtA$_2$(lactate)$_2$] are summarized in Table II.

No. 3, p. 856 (1977), listed the lactate complex of diaminocyclohexane platinum(II), cis-[Pt(DAXHXN)(lactate)$_2$], and gave an M (figure of merit) of 22 against Leukemia L1210 for this compound against 3.3 for cis-[Pt(NH$_3$)$_2$Cl$_2$]; where, $$M = \frac{LD_{50} \times \text{Best } \%ILS}{ID_{99.9} \times 100}$$

When the cis-[Pt(DACHXN)(lactate)$_2$] of the prior art was tested along with the platinum lactate complexes of the present invention for comparison purposes, it was found to be most active at 25 mg/kg and toxic at 100 mg/kg.

In the above publication, no solubility data was given. Cis-[Pt(DACHXN)(lactate)$_2$] prepared according to the process of this invention was less soluble in water than 0.1 g/100 ml, which is much less than the solubilities of the platinum amine lactate complexes of this invention (greater than 10 g/100 ml of water when freshly prepared). Low water solubility greatly reduces the utility of the compound for oral or intravenous administration.

If the active and toxic doses observed for these compounds are "normalized" in terms of the platinum content of each compound, wide differences in active and toxic doses are still observed. Differences in platinum content resulting from different amine ligands do not explain differences in active and toxic doses.

Cis-[Pt(NH$_3$)$_2$(lactate)$_2$] was also tested against L1210 lymphoid leukemia in mice through the National Cancer Institute. The results of this test are summarized in Table III.

TABLE II

Anti-Tumor Screening Data for cis-[PtA$_2$(C$_3$H$_5$O$_3$)$_2$] vs. the S180 Ascites Tumor System

| Compound | Medium | Dose (a) (mg/kg) | % ILS | 30-Day Survivors | Positive % (b) ILS | Control 30-Day Survivors |
|---|---|---|---|---|---|---|
| Example 1 (A=NH$_3$) | Water | 15 | 100 | 4/4 | 77 | 3/6 |
|  |  | 30 | 100 | 4/4 |  |  |
|  |  | 60 | −66 | 0/4 |  |  |
|  |  | 120 | −76 | 0/4 |  |  |
| Example 2 (A=CH$_3$NH$_2$) | Water | 15 | 47 | 0/4 | 78 | 2/6 |
|  |  | 30 | 50 | 2/4 |  |  |
|  |  | 60 | 76 | 1/3 |  |  |
|  |  | 120 | 100 | 2/4 |  |  |
| Example 3 (A=en) | Water | 20 | 100 | 4/4 | 81 | 3/6 |
|  |  | 40 | 100 | 4/4 |  |  |
|  |  | 80 | 63 | 3/4 |  |  |
|  |  | 160 | −71 | 0/4 |  |  |

(a) 4 mice/dose
(b) Positive control = 8 mg/kg cis-[Pt(NH$_3$)$_2$Cl$_2$] in saline.

All compounds were administered as aqueous solutions. All show excellent activity against this tumor system, at different dose levels.

Cis-[Pt(NH$_3$)$_2$(lactate)$_2$] is highly active at 15 and 30 mg/kg and is toxic at 60 mg/kg.

Cis-[Pt(CH$_3$NH$_2$)$_2$(lactate)$_2$] is considerably less potent as an anti-tumor agent than the NH$_3$ analog, with a threshold of activity at ca. 30 mg/kg and excellent activity at 120 mg/kg. The toxic level was not reached.

[Pt(en)(lactate)$_2$] is highly active at 20 and 40 mg/kg and toxic at 160 mg/kg.

Ridgeway et al., in the "Proceedings of the Third International Symposium on Platinum Coordination Complexes in Cancer Chemotherapy" held in October 1976, at the Wadley Institute and reported in J. of Clinical Hematology and Onocology, 7, No. 1, P. 225 and

TABLE III

Anti-Tumor Screening Results vs. the L1210 Tumor System

| Compound | Dose Regimen[a] | Dose (mg/kg) | T/C[b] | Toxicity;[d] Survivors/Total |
|---|---|---|---|---|
| Cis-[Pt(NH$_3$)$_2$ (lactate)$_2$] | Day 1, 5, 9 | 120 | T[c] | 2/6 |
|  | 60 | 114 | 6/6 |  |
|  |  | 30 | 138 | 6/6 |
|  |  | 15 | 108 | 6/6 |
|  |  | 7.5 | 100 | 6/6 |

[a]Dose Regimen: Doses administered on Days 1, 5 and 9.
[b]T/C: [Mean life span (test)/Mean life span (control)] × 100.
[c]T: Toxic by NCI criteria (Geran, et al. "protocols for screening Chemical Agents and Tumors and Other Biological Systems," Cancer Chemotherapy Report, Part 3, 3rd. ed., Summer, 1972).
[d]Toxicity: This refers to the number of survivors on day 5.

The cis-[Pt(NH$_3$)$_2$(lactate)$_2$] showed peak activity at 30 mg/kg (T/C: 138), in agreement with the S180a results. By comparison, the NCI's cis-[Pt(NH$_3$)$_2$Cl$_2$] positive control shows a maximum T/C of 152 at 5.0 mg/kg using the Day 1, 5 and 9 dose regimen.

What is claimed is:

1. A pharmaceutical composition for use in treating malignant animal tumor cells sensitive to cis-[Pt(II)A$_2$(C$_3$H$_5$O$_3$)$_2$] which comprises said cis-[Pt(II)A$_2$(C$_3$H$_5$O$_3$)$_2$] wherein Pt is in valence state II and is coordinated to A in a cis configuration, A is ammonia or a monodentate alkylamine or A$_2$ is a bidentate alkylenediamine, and C$_3$H$_5$O$_3$ is a lactate anion in combination with a non-toxic pharmacologically acceptable inert carrier or diluent.

2. The composition of claim 1 wherein the active ingredient is selected from the group consisting of cis-diammineplatinum(II) lactate and cis-bis(lower alkylamine)platinum(II) lactate.

3. The composition of claim 2 wherein the active ingredient is cis-diammineplatinum(II) lactate.

4. The composition of claim 2 wherein the active ingredient is cis-bis(lower alkylamine)platinum(II), lactate.

5. The composition of claim 4 wherein the active ingredient is cis-bis(methylamine)platinum(II) lactate.

6. The composition of claim 1 wherein the active ingredient is lower alkylenediamineplatinum(II) lactate.

7. The composition of claim 6 wherein the active ingredient is ethylenediamineplatinum(II) lactate.

8. The composition of claim 1 in a form suitable for parenteral administration.

9. The composition of claim 1 in a form suitable for oral administration.

10. The composition of claim 9 in the form of a tablet.

11. The composition of claim 9 in capsule form.

12. The composition of claim 1 wherein the active ingredient is present in unit dosage form in an amount of from about 4–300 mg.

13. A method of treating malignant animal tumor cells sensitive to cis-[Pt(II)A$_2$(C$_3$H$_5$O$_3$)$_2$] which comprises administering to an animal afflicted with said tumor cells an amount of cis-[Pt(II)A$_2$(C$_3$H$_5$O$_3$)$_2$] sufficient to cause regression of the animal tumor cells, wherein Pt is in valance state II and is coordinated to A in a cis configuration, A is ammonia or a monodentate alkylamine or A$_2$ is a bidentate alkylenediamine, and C$_3$H$_5$O$_3$ is a lactate anion.

14. The method of claim 13 wherein said complex is selected from the group consisting of cis-diammineplatinum(II) lactate and cis-bis(lower alkylamine)platinum(II) lactate.

15. The method of claim 14 wherein said complex is cis-diammineplatinum(II) lactate.

16. The method of claim 14 wherein said complex is cis-bis(lower alkylamine)platinum(II) lactate.

17. The method of claim 16 wherein said complex is cis-bis(methylamine)platinum(II) lactate.

18. The method of claim 13 wherein said complex is lower alkylenediamineplatinum(II) lactate.

19. The method of claim 18 wherein said complex is ethylenediamineplatinum(II) lactate.

20. The method of claim 13 wherein said complex is administered parenterally.

21. The method of claim 13 wherein said complex is administered orally.

22. The method of claim 13 wherein said complex is administered in a single dose.

23. The method of claim 13 wherein said complex is administered in multiple doses.

* * * * *